United States Patent [19]

Silvestrini et al.

[11] 4,451,477

[45] May 29, 1984

[54] BENDAZAC TREATMENT OF CATARACT

[75] Inventors: Bruno Silvestrini; Leandro Baiocchi, both of Rome, Italy

[73] Assignee: Aziende Chimiche Riunite Angelini Francesco A.C.R.A.F. S.p.A., Rome, Italy

[21] Appl. No.: 386,468

[22] Filed: Jun. 8, 1982

[30] Foreign Application Priority Data

Nov. 27, 1981 [IT] Italy ................ 49790 A/81

[51] Int. Cl.³ .......................... A61K 31/415
[52] U.S. Cl. ............................... 424/273 N
[58] Field of Search ..................... 424/273 N

[56] References Cited

U.S. PATENT DOCUMENTS

| Re. 27,253 | 12/1971 | Palazzo | 424/273 N |
| 3,625,970 | 12/1971 | Ambrus | 424/273 N |
| 4,282,237 | 8/1981 | Silvestrini | 424/273 N |
| 4,352,813 | 10/1982 | Silvestrini et al. | 424/273 N |

OTHER PUBLICATIONS

G. Boschi et al., "L'uso del bendazac lisina (Bendalina) nella terapia della cataratta," Minerva Oftalmologica 24, Reprint (1982) (English Summary).

R. Leoni et al., "Esperienze con Bendalina nella terapia della cataratta," Minerva Oftalmologica 24, reprint (1982) (English Summary).

Michele Testa et al., "Pilot Study of Bendazac for Treatment of Cataract," The Lancet, pp. 849–850 (Apr. 10, 1982).

S. Peralta et al., "Saggio clinico-terapeutico della Bendalina nella cataratta," Il Policlinico–Sez. Medica 89, Reprint (1982).

*Primary Examiner*—Douglas W. Robinson
*Attorney, Agent, or Firm*—Ladas & Parry

[57] ABSTRACT

It was discovered that bendazac, or [(1-benzyl-1H-indazol-3-yl)oxy] acetic acid, when administered in a form suitable to obtain therapeutic tissue concentrations, determines a regression of cataract. It was demonstrated in particular, that the lysine salt of bendazac is well adapted for this use since it produces adequate tissue concentrations following both oral administration and topical application on the eye. The chemical and physical characteristics of this bendazac salt are described here together with the preparation techniques.

11 Claims, No Drawings

BENDAZAC TREATMENT OF CATARACT

RELATED APPLICATION

Related to this invention is U.S. application Ser. No. 269,923 filed on June 2, 1981 now U.S. Pat. No. 4,352,813.

BACKGROUND OF INVENTION

Cataract is a disease of the eye consisting in opacification of the lens, a bioconvex body interposed between the anterior chambers and the vitreous body of the eye. The lens has the function of focusing the light rays on the retina where they are perceived and transmitted to the brain in the form of visual impulses. Cataract is, thererefore, accompanied by a decrease in visual capacity, which in the more severe cases leads to blindess. To indicate the medical and social importance of this disease it sufficient to remember that senile cataract affects 4.6 percent of the population between years 52 and 64, 18 percent aged between 65 and 74 and 46 percent aged between 75 and 85 years (Kini et al., 1978).

The lens is surrounded by a collagenous elastic capsule containing fiber cells; its main component is a homogeneous, transparent protein gel which has the same function as the glass in the artificial lens. With increasing age or due to a variety of different factors (diabetes and other metabolic disturbances, traumas, X-rays, toxic substances including certain drugs, etc.). The lens fibers become opaque and loose thier transparency. Until recently these changes were considered irreversible. It was generally believed that the only possible cure for cataract was surgical removal of the lens which was then substituted with external or internal artificial lens implanted behind the eye (Nevyas, 1980). The only good results reported with some pharmacological treatment were a possible slowdown in cataract development. This is, for example, the case of Catalin or 1-hydroxy-5-oxo-5H-pyrido[3,2-a]phenoxazino-3-carboxylic acid (Hayashi et al., 1979) and of aspirin or acetylsalicylic acid (Cotlier and Sharma, 1980). The mechanism of action of this compound was thought to be due to the lowering of serum tryptophan levels or to the inhibition of o-diphenoloxidase (Prabhakaran, 1981).

Research performed during the past few years have demonstrated that lens opacification is associated with a denaturation of the transparent protein gel making up the lens (Davson, 1980). In cataract there is an increased production of giant macromolecules consisting of aggregate subunits linked by disulfide bonds which tend to precipitate. These bonds are covalent in nature and can be divided by the proteolytic enzymes physiologically present in the tissues. The activity of these enzymes therefore account for the ability of the lens to maintain its transparent nature throughout life despite the fact that it is continuously exposed to the action of exogenous or endogenous agents capable of producing denaturation and aggregation of the lens proteins. Lens opacification occurs when the protein denaturation exceeds the defensive capacities of the enzymes in the lens. These considerations could suggest the use of certain enzymes in the treatment of cataract. This idea is however difficult to put into practice because these substances very rarely penetrate through the biological membrane and also because our present knowledge is insufficient to prepare suitably specific enzymes for the above lens protein aggregates.

The basic idea of this discovery was instead that of using a substance capable of slowing the phenomena of lens protein denaturation causing opacification, and allowing the natural enzymes present in this tissue to adequately act on aggreates already formed. In other words, we proposed to improve the correlation between the enzymatic defense mechanisms of the lens and the intensity of the phenomena of protein aggregation, presuming that in this manner it would be theoretically possible to obtain the physiological regression of cataract.

To put this idea into practice we decided to take advantage of the experience accumulated in past researches performed on protein denaturation and its possible prevention with anti-denaturant drugs. These investigations demonstrated that different antiinflammatory drugs posses an anti-denaturant activity on proteins (for a review on the subject see Mizushima, 1968 and Silvestrini, 1968). These substances are, however, too specific and too toxic to be employed for this use; on the other hand, we have already mentioned that studies performed with acetylsalicylic acid have shown that this substance delays the development of cataract but does not determine its regression (Cotlier and Sharme, 1980). What appeared potentially suited for this use was instead bendazac a drug with a very specific anti-denaturant activity on some blood proteins (Silvestrini et al. 1969, 1969a and 1970). It was necessary, however, to find out whether or not this substance also acted on lens proteins; the problem of its oral absorption in man also had to be solved since on the basis of past investigations oral absorption resulted too low (Silvestrini et al., 1969).

PRIOR ART

Bendazac is the object of Italian patent application No. 19723 filed on Aug. 29, 1966 and subsequently filed in other countries, including the U.S.A. The corresponding Italian Patent No. 1,043,762 was granted on Feb. 29, 1980 and the U.S. Pat. No. 3,470,194 granted on Sept. 30, 1969. The anti-denaturant properties of bendazac are mentioned in these patents but no mention or hypothesis is made whatsoever on its healing effect on cataract.

There does not exist any anti-cataract drug in literature which in any way resembles bendazac.

EXPERIMENTAL

Experiments in vitro: A study was performed on both lens homogenates and intact lens. The opacification of this material was obtained by heating. For this purpose the same method as that already employed to study blood proteins was used (Silvestrini et al., 1968; Silvestrini et al., 1970) with some minor modifications which are reported below.

For the study of the homogenate, fresh rat lens were used which has been removed from the capsule, immersed in phosphate buffer (pH 7.5; 0.1M) in the volumetric ratio of 15:85 and then homogenated. The homogenate was then centrifuged (10 minutes at 4000 r.p.m.), the supernatant was collected and further diluted 1:1 with the above phosphate buffer, alone or containing bendazac at different concentrations. The solution thus obtained was heated at 60° C. for 20 minutes and the denaturation was assessed nephelometrically. The results obtained are reported in Table 1. As reference a comparison is made with the values obtained with bovine serum albumin (BSA) denaturation.

TABLE 1

Protective activity of bendazac on heat-induced denaturation of lens homogenate and BSA.

| | % inhibition of bendazac Drug molar concentration | | |
|---|---|---|---|
| | $10^{-3}$ | $5 \times 10^{-4}$ | $10^{-4}$ |
| lens homogenate | 68 | 32 | 18 |
| BSA | 60 | 47 | 12 |

The results obtained demonstrate that bendazac prevents heat-induced denaturation of lens homogenate and that this protective effect is similar to that observed with BSA. The experiment was repeated using different salts of bendazac including lithium, sodium, potassium, ammonium, organic bases (such as ethylenediamine, piperazine and diisopropylamine) and lysine. At the same molar concentrations, all these salts exerted the same anti-denaturant effect on the lens homogenate as that of bendazac alone. This experiment proves that the active ingredient is bendazac. The intact lens was studied by using fresh bovine lens which were kept for 2 hours in the phosphate buffer described above, either alone or containing bendazac at different concentrations. The lenses were then heated at 50° C. for 120 minutes; this procedure produced a clear-cut opacification in the subcapsular region. The degree of opacification was assessed blindly (the experimentor was unaware of the treatment), using a score from 0 to 4. The results obtained are given in Table 2.

TABLE 2

Protective activity of bendazac on heat-induced opacification of isolated bovine lenses.

| | Degree of opacification Bendazac molar concentrations | | | |
|---|---|---|---|---|
| | 0 | $10^{-3}$ | $10^{-4}$ | $10^{-5}$ |
| without heating | — | — | — | — |
| control with heating | ++++ | + | ++ | +++ |

Bendazac exerts a clearcut protective effect on this experimentally induced cataract even though the concentrations are higher than those active in the previous experiment. The test was repeated using the various salts of bendazac mentioned above and in this case also with the same molar concentrations the results obtained were identical to those observed with bendazac alone.

Investigations on oral absorption in man of the lysine salt of bendazac

It is known in literature that the oral absorption of bendazac in humans is rather low; following 8 days of treatment with bendazac at increasing does ranging from 150 to 900 mg daily the blood levels of the product were found to be 8 mcg (Silvestrini et al., 1968). These blood levels appeared too low to obtain therapeutic activity. We have now found that the lysine salt of bendazac is better absorbed in man than bendazac alone; as will be further pointed out in the Chemistry section, this lysine salt is a bihydrate. As shown in Table 3, after a single oral administration of 500 mg of lysine salt of bendazac, corresponding to 303.8 mg of bendazac, the mean serum concentration found in 6 volunteers 2 hours after administration was 30 mcg/ml; under the same conditions the serum levels obtained with 300 mg of bendazac alone were 8 mcg/ml. These results demonstrate that the lysine salt of bendazac is a form suitable to obtain effective tissue concentrations.

Study on the anti-cataract activity in humans

A first experiment was conducted on 24 patients with different types of cataract (cortical; corticonuclear, posterior subcapsular). The patients' medical history showed that their cataract was rapidly progressing. The experiment included an examination of vision, refraction and slit-lamp test; the investigator was asked to express an overall judgement. These evaluations were performed before the beginning of treatment, after 4 weeks and again at the end of treatment when prolonged. The lysine salt of bendazac was administered at the dose of 1500 mg (corresponding to 911.5 mg of bendazac) divided into three daily administrations during meals. The average duration of treatment was 50.4 days with time limits from 28 to 86 days. The study group consisted of 11 females and 13 males with an average age of 59.5 (47–74). The effects of treatment are summarized in Table 3; the values obtained in each patient are illustrated instead in Table 4. For practical purposes the results are expressed as: improvement (+), no change (0), worsening (−).

TABLE 3

Summary of the results obtained in the first experiment conducted with the lysine salt of bendazac in cataract.

| Evaluation | Vision | Refraction | Slit-lamp and/or Transillum. | Overall Judgement |
|---|---|---|---|---|
| improvement (+) | 18 | 10 | 14 | 18 |
| no change (0) | 6 | 13 | 10 | 5 |
| worsening (−) | — | 1 | — | 1 |

TABLE 4

Details on each patient used in the first experiment conducted with the lysine salt of bendazac in cataract

| No. cases | Name | Age | Sex | Type of cataract | Days treatment | Vision | Refraction | Slit-lamp and/or transillumin. | Overall Judgement | Note |
|---|---|---|---|---|---|---|---|---|---|---|
| 1 | V. C. | 47 | F | subcapsular | 63 | + | 0 | + | + | |
| 2 | S. E. | 51 | F | cortical | 28 | + | + | + | + | |
| 3 | I. A. | 53 | F | cortical | 78 | + | + | + | + | |
| 4 | F. A. | 55 | M | cortical | 33 | + | + | + | + | |
| 5 | D. M. | 56 | M | cortico-nuclear | 84 | + | 0 | + | + | |
| 6 | D. A. P. | 58 | M | cortico-nuclear | 72 | + | + | 0 | + | |

TABLE 4-continued

Details on each patient used in the first experiment conducted with the lysine salt of bendazac in cataract

| No. cases | Name | Age | Sex | Type of cataract | Days treatment | Vision | Refraction | Slit-lamp and/or transillumin. | Overall Judgement | Note |
|---|---|---|---|---|---|---|---|---|---|---|
| 7 | A. M. | 63 | F | cortical | 79 | + | + | 0 | + | |
| 8 | A. C. | 65 | M | subcapsular | 35 | 0 | — | 0 | — | |
| 9 | T. D. | 66 | M | subcapsular | 34 | + | 0 | + | + | |
| 10 | A. C. | 66 | F | subcapsular | 33 | + | + | + | + | |
| 11 | C. M. | 67 | F | subcapsular | 65 | + | 0 | + | + | |
| 12 | C. L. | 67 | M | cortical | 54 | + | + | 0 | + | |
| 13 | T. A. | 68 | M | cortical | 31 | + | + | 0 | + | |
| 14 | B. C. | 68 | F | cortico-nuclear | 61 | + | + | + | + | |
| 15 | P. A. | 69 | M | cortical | 35 | 0 | 0 | + | 0 | |
| 16 | A. G. | 69 | M | subcapsular | 86 | + | 0 | + | + | |
| 17 | C. R. | 73 | F | cortical | 49 | + | + | + | + | |
| 18 | I. G. | 73 | M | subcapsular | 73 | 0 | + | + | + | |
| 19 | A. C. | 51 | M | subcapsular | 54 | + | 0 | 0 | 0 | |
| 20 | G. A. | 73 | F | cort.-nucl. | 29 | + | + | 0 | + | |
| 21 | LRN | 58 | M | subcapsular | 35 | 0 | 0 | 0 | 0 | diabetes |
| 22 | F. G. | 74 | F | cort.-nucl. | 72 | 0 | 0 | 0 | 0 | " |
| 23 | M. E. | 50 | F | subcapsular | 29 | 0 | + | 0 | 0 | " |
| 24 | G. F. | 63 | M | subcapsular | 29 | + | 0 | + | + | " |

In this experiment the lysine salt of bendazac produced an improvement in a high number of patients (10–18, depending on the evaluation method), whereas only 1 patient showed a worsening effect. Relatively poor results were obtained in 5 patients, one of whom was a diabetic.

As a result of these encouraging results we decided to repeat the experiment under double blind conditions comparing the lysine salt of bendazac with placebo. A total of 35 patients were used; 19 were treated with placebo and 16 with the lysine salt of bendazac. The experimental methods used were identical to those described in the first experiment except for the duration of treatment which was always 4 weeks. The results are summarized in Table 5. The values obtained in each patients are instead reported in Table 6.

TABLE 5

Summary of the results obtained in the second experiment conducted with the double blind method to study the activity of bendazac in cataract.

| No. cases | Sex | Type of cataract | Treatment | Evaluation | Vision | Refraction | Slit-lamp | Trans-illumination | Overall Judgement |
|---|---|---|---|---|---|---|---|---|---|
| 19 | 12 F 7 M | cortical cortico-nuclear | 13 Placebo 6 | (+) (0) (−) | 1 6 12 | 1 12 6 | — 2 9 | — 1 6 | 1 2 16 |
| 16 | 14 F 2 M | cortical cortico-nuclear | 13 Bendazac lysine 3 salt | (+) (0) (−) | 10 6 — | 9 7 — | 10 2 1 | 4 2 — | 11 3 2 |

TABLE 6

Details on each patient used in the second experiment conducted with the double blind method to study the activity of bendazac in cataract.

| No. of cases | Name | Sex | Type of cataract | Treatment | Vision | Refraction | Slit-lamp | Transillumination | Overall Judgement |
|---|---|---|---|---|---|---|---|---|---|
| 1 | P. A. | F | cortico-nuclear | placebo | — | 0 | | | — |
| 4 | L. G. C. | M | cortical | placebo | + | + | 0 | | + |
| 6 | M. M. | F | cortico-nuclear | placebo | — | — | | — | — |
| 8 | F. P. | F | cortical | bendazac L | 0 | 0 | | | 0 |
| 9 | L. O. | F | cortico-nuclear | placebo | — | — | | | — |
| 10 | M. M. | F | cortico-nuclear | bendazac L | + | 0 | + | + | + |
| 11 | S. M. | F | cortical | placebo | 0 | 0 | | | 0 |
| 12 | C. P. | M | cortical | placebo | — | 0 | | | — |
| 13 | L. V. | F | cortical | bendazac L | + | 0 | + | | + |
| 14 | S. K. | M | cortical | placebo | — | 0 | — | | — |
| 15 | F. F. | F | cortical | bendazac L | 0 | 0 | 0 | 0 | 0 |
| 16 | G. A. | F | cort. nucl. | bendazac L | 0 | 0 | — | | — |
| 17 | P. E. | F | cortical | bendazac L | + | + | + | | + |
| 18 | C. G. | F | cort. nucl. | placebo | — | 0 | — | — | — |

TABLE 6-continued

Details on each patient used in the second experiment conducted with the double blind method to study the activity of bendazac in cataract.

| No. of cases | Name | Sex | Type of cataract | Treatment | Vision | Refraction | Slit-lamp | Transillumination | Overall Judgement |
|---|---|---|---|---|---|---|---|---|---|
| 19 | A. R. | F | cortical | bendazac L | + | + | + |  | + |
| 20 | T. D. | M | cort. nucl. | placebo | − | − |  |  | − |
| 21 | C. L. | M | cortical | placebo | − | 0 |  |  | − |
| 23 | C. I. | F | cortical | placebo | − | 0 | − | − | − |
| 24 | C. L. | F | cortical | bendazac L | 0 | + |  | + | + |
| 25 | A. A. | F | cortical | placebo | 0 | 0 | − | − | − |
| 26 | V. F. | M | cortical | placebo | − | 0 |  |  | − |
| 27 | D. S. D. | F | cortical | bendazac L | + | + | + |  | + |
| 28 | F. C. | M | cortical | placebo | 0 | 0 | 0 | 0 | 0 |
| 29 | M. R. | F | cortical | bendazac L | 0 | + | + | + | + |
| 30 | M. A. | M | cort. nucl. | bendazac L | + | 0 | 0 | 0 | 0 |
| 31 | T. A. | F | cortical | placebo | 0 | − | − | − | − |
| 32 | L. C. | F | Cortical | placebo | 0 | 0 | − | − | − |
| 33 | D. A. L. | F | cortical | bendazac L | + | + | + | + | + |
| 34 | G. A. | F | cortical | placebo | 0 | − | − |  | − |
| 35 | E. D. | F | cortical | bendazac L | + | + | + |  | + |
| 36 | P. A. | F | cortical | bendazac L | 0 | 0 | − |  | − |
| 37 | C. M. | F | cortical | placebo | − | 0 | − |  | − |
| 38 | A. M. | M | cortical | bendazac L | + | + | + |  | + |
| 39 | V. P. | F | cort. nucl. | placebo | − | − |  |  | − |
| 40 | P. E. | F | cortical | bendazac L | + | + | + |  | + |

This second study confirmed without any doubt that the administration of the lysine salt of bendazac has a healing effect on cataract.

Finally, bendazac was administered in 4 patients in the form of eye drops containing 0.25% of the lysine salt of bendazac. Eye drops were instilled 3 times daily for one month. Even in this group of patients a clear-cut regression of the cataract was observed.

CONCLUSIONS

The data reported here demonstrate that bendazac alone or in the form of different salts exerts a protective action in vitro with respect to lens opacification. In humans the lysine salt of bendazac showed to be particularly suited to obtain the therapeutic effects desired because of its good oral absorption. Furthermore, in patients with cataract, this compound induces a regression of the disease after both oral administration and topical application on the eye. This discovery is of the utmost medical importance since it opens completely new perspectives for the treatment of cataract.

Accordingly this invention provides a method for the treatment of cataracts in a human comprising administering to said human an effective amount of bendazac. The bendazac may be administered orally and preferably said bendazac is adminstered in a quantity sufficient to achieve an effective blood level of 20–40 μg/ml in the range of 455 to 1824 mg per day in an acceptable pharmaceutical form suitable to obtain effective tissue concentrations.

As a preferred embodiment said bendazac is administered in the form of its lysine salt hydrate at a dosage of 750 to 3000 mg per day. This dosage may perferably be administered subdivided in 2 or more doses per day.

Bendazac may also preferably be adminstered directly to the affected eye for the treatment of cataracts. When administered directly to the eye a preferred procedure is to adminster the bendazac in the form of a composition comprising an acceptable pharmaceutical carrier having bendazac in concentration in the range of 0.1–1 percent. When the bendazac pharmaceutical composition is used a preferred procedure for the treatment of cataract is one in which said bendazac is administered 2 or 3 times a day, in the quantity of 3 drops for each application and it is also preferred where said bendazac is administered in the form of its lysine salt hydrate.

CHEMISTRY

In order to obtain the bendazac salt with lysine the preparation is performed by heating, preferably in ethanol or water-acetone, equimolecular quantities of [(1-benzyl-1H-indazol-3-yl)oxy]acetic acid and the aminoacid. The salt crystallizes on cooling as a bihydrate.

The so obtained salt can be used as such or after drying under vacuum to constant weight. Both the bihydrate and the anhydrous salts with one or the other optically active forms of lysine as well as the salt with racemic lysine can be employed in different pharmaceutical forms.

In use, the compound of the invention is administered orally in conventional formulations, namely in association with pharmaceutical excipients generally used for the production of compositions for oral administration. Doses between 0.3 g and 1.5 g have to be administered daily, eventually divided in 2 or more administrations.

Conventional pharmaceutical compositions for oral administration may be used such as tablets and capsules; the unit dose for both table and capsule of active ingredient may be 100–500 mg.

The carriers used in the preparation of these compositions are the excipients known in the pharmacist art. In the preparation of tablets, typical excipients include disintegrating agents, e.g., maize starch and lubricant agents e.g., magnesium stearate; in the preparation of capsules, standard gelatin capsules may be used containing the active ingredient alone or mixed with a diluent.

Also in topical applications on the eye the compound will be used in conventional eye drop form, well known to people skillful in the art.

The following non-restrictive examples illustrate the preparation of the salt which is the subject of the present invention.

EXAMPLE 1

Salt of [(1-benzyl-1H-indazol-3-yl)oxy]acetic acid with L. lysine (dihydrate).

12 g (0.042 mol) of [(1-benzyl-1H-indazol-3-yl)]oxy acetic acid and 6.2 g (0.042 mol) of L. lysine were dissolved in 100 ml of 95% ethanol by heating. The mixture was filtered warm in order to remove the very small amounts of impurities and it was then left to stand overnight at room temperature. The crystalline product was filtered and recrystallized from 95% ethanol: 15 g of the salt was first obtained (yield 75.9%) while from the mother-liquor another quantity of product was obtained by partially evaporating the solvent. The product showed a melting point at 178–81° C. with loss of water during heating.

EXAMPLE 2

The salt obtained according to the Example 1 was dried under vacuum (5–10 Torr.) at 105° C. to constant weight: also in this form it shows a melting point at 178–81° C. with decomposition.

BIBLIOGRAPHY

KINI, M.M., LEIBOWITZ, H.M., COLTON, J., NICKERSON, R.J., GANLEY, J., DAWBER, T.R., Am. J. Ophthalmol 85, 28, 1978.

NEVYAS H.J., Ocular Size and Shape, Regulation During Development. (eds., Hilfer S.R. and Sheffield J.B.), Springer-Verlag, New York, pp 189–207, 1980.

HAYASHI, H. and NISHIDA, T., The Folia Ophthalmologica Japonica, Vol. 30, No. 4, 1979.

COTLIER, E. and SHARME, Y.R., Lancet, i, 607, 1980.

PRABHAKARAN, K., Pathology, 9, 928, 1981.

DAVSON, H., Physiology of the Eye, 4th Edition, Academic Press, New York, pp 116–164, 1980.

MIZUSHIMA, Y., In: Inflammation, Proc. Int. Symp., Bologna 1967. Eds., Silvestrini, B., Tura, S. and Spector, W.G., Excerpta Medica Foundation, Amsterdam, pp 37–43, 1968.

SILVESTRINI, B., In: Inflammation, Proc. Int. Symp., Bologna 1967, Eds., Silvestrini, B., Tura, S. and Spector, W.G., Excerpta Medica Foundation, Amsterdam, pp 26–36, 1968.

SILVESTRINI, B., CIOLI, V. and BURBERI, S., Arzneim. Forsch. 19, 30–36, 1969.

SILVESTRINI, B., CATANESE, B., and LISCIANI, R., In: Inflammation Biochemistry and Drug Interaction., Proc. Int. Symp., Como, 1968. Eds., Bertelli, A., Houck, J.C., Excerpta Med. Foundation, Amsterdam, pp 283–288, 1969.

SILVESTRINI, B., CATANESE, B., LISCIANI, R. and ALESSANDRONI A., Arzneim. Forsch. 20, 250–253, 1970.

We claim:

1. A method for the treatment of cataracts in a human comprising administering to said human a therapeutically effective amount of bendazac.

2. A method for the treatment of cataracts according to claim 1, wherein said bendazac is administered orally.

3. A method for the treatment of cataracts according to claim 2, wherein said bendazac is administered in a quantity sufficient to achieve an effective blood level of 20–40 μg/ml in the range of 455 to 1824 mg per day in an acceptable pharmaceutical form suitable to obtain effective tissue concentrations.

4. A method for the treatment of cataracts according to claim 3, wherein said bendazac is administered in the form of a lysine salt.

5. A method for the treatment of cataracts according to claim 4, wherein said bendazac lysine salt is administered at a dosage of 750 to 3000 mg per day.

6. A method for the treatment of cataracts according to claim 5, wherein said bendazac lysine salt is administered subdivided in 2 or more doses per day.

7. A method for the treatment of cataracts according to claim 1, wherein said bendazac is administered directly to the affected eye.

8. A method for the treatment of cataracts according to claim 7, wherein said bendazac is administered in the form of an acceptable pharmaceutical carrier in concentration in the range of 0.1–1 percent.

9. A method for the treatment of cataracts according to claim 8, in which said bendazac is administered 2 to 3 times a day, in the quantity of 3 drops for each application.

10. A method for the treatment of cataracts according to claim 7, in which bendazac is administered in the form of a lysine salt.

11. A method for treatment of cataracts according to claim 1 wherein said bendazac is in the form of a pharmaceutically acceptable salt.

* * * * *